United States Patent [19]

Brooks

[11] Patent Number: 4,995,379

[45] Date of Patent: Feb. 26, 1991

[54] INSTANT FACE LIFT

[76] Inventor: Joan Brooks, 6594 Bellaire Dr., New Orleans, La. 70124

[21] Appl. No.: 322,174

[22] Filed: Mar. 13, 1989

[51] Int. Cl.⁵ .............................................. A61F 5/00
[52] U.S. Cl. ................................. 128/76 B; 128/76 R
[58] Field of Search ............................ 128/76 R, 76 B

[56]  References Cited
U.S. PATENT DOCUMENTS

| | | | |
|---|---|---|---|
| 1,321,137 | 11/1919 | Morgan | 128/76 B |
| 2,068,777 | 1/1937 | Teal | 128/76 B |
| 2,863,448 | 12/1958 | Giusti | 128/76 R |
| 2,896,613 | 7/1959 | Brown | 128/76 R |
| 3,524,443 | 8/1970 | Batlin | 128/76 B |
| 3,672,363 | 6/1972 | Masters | 128/76 B |
| 3,695,257 | 10/1972 | Hale | 128/76 B |
| 3,736,925 | 6/1973 | Erman | 128/76 B |
| 4,239,037 | 12/1980 | Fausone | 128/76 B |
| 4,823,778 | 4/1989 | Ewing | 128/76 B |

Primary Examiner—William Pieprz
Assistant Examiner—Tonya Lamb

[57]  ABSTRACT

A device to provide a face lift without surgery comprising one member securely attached to a user's head and a second member slidingly attached to the first member with the second member have two ends each end being attachable to the face or other part of the head of the wearer with tension adjusting means as a part of the second member.

4 Claims, 1 Drawing Sheet

INSTANT FACE LIFT

BACKGROUND OF THE INVENTION

The invention relates to a face lift device which does not require surgery. It comprises a tensioned strap which is placed on the head and has ends adhesively attached to the wearer's face. The basic idea is old as is shown in U.S. Pat. Nos. 3,782,372 and 4,239,037. The prior art devices produce an unnatural look because when the head is moved one side of the face will appear tighter than the other side.

SUMMARY OF THE INVENTION

The object of the invention is to provide a face lift device which is more natural looking, more comfortable to wear, and automatically adjusts to movements by the wearer.

The above advantages are accomplished by the provision of two bands, one of which is slidable with respect to the other. These bands are both attached to the head of the wearer and the slidable feature gives the more natural and more comfortable look. The invention also uses lighter weight material than has been used in the past providing greater comfort.

DETAILED DESCRIPTION OF PREFERRED EMBODIMENTS

Figures 1, 2:
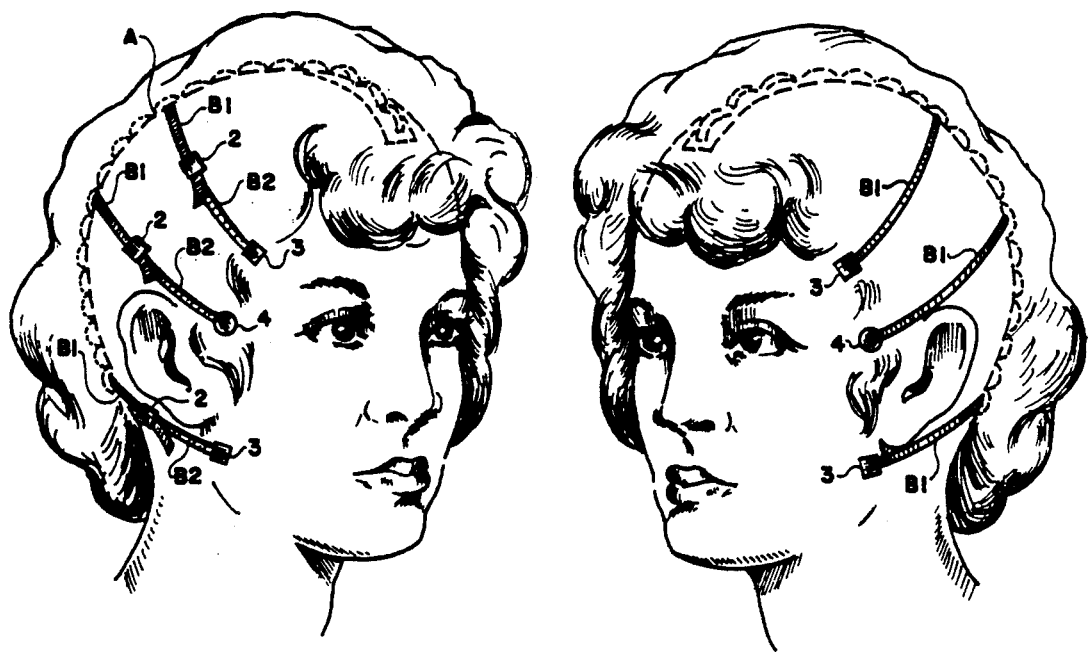
FIGS. 1 and 2 show the invention as worn.
Figure 3:
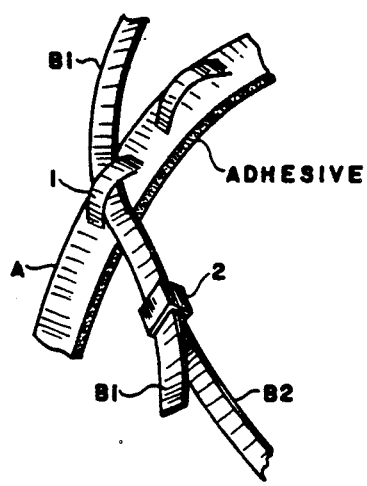
FIG. 3 shows an enlargement of the loops 1 on band A.

FIG. 1 shows the preferred embodiment of the invention. Element A is a band which is adhesively attached to the scalp of the user. It is formed of a light weight strong flexible material. A light weight plastic mesh is preferred. It can be approximately an eighth of an inch or less. A plurality of loops 1 are integral parts of the band A. These are provided along the length of the band so that an element passed through a loop would be perpendicular to the band. Element A is attached to the head of the user by an adhesive, which can be surgical glue or any non-allergic adhesive.

Elements B1 and B2 are straps which can be made of filamentary material such as plastic. Numerals 3 are tabs which are designed to be adhesively attached to the head of the user, usually to the skin of the face. Each strap has a tab 3 on one of its ends. The tabs can be of any desired shape. A wider tab spreads out the pull on the skin; a narrower and longer tab pulls upward more strongly. The shape of the tab can be chosen for the desired effect. The strap B1 has its end opposite tab 3 shaped to pass through one of the loops 1. After the tabs 3 are adhesively attached to the user's head, the end of B1 is slid through the loop and through a locking member 2 which is attached to the end of B2 which does not have a tab 3. The end of B1 is pulled until the desired tension is reached, then it is locked in position. The locking tab 2 can be any known locking means.

To make the device as inconspicuous as possible, the elements are either completely transparent or flesh color. A, in particular could be the color of hair.

As can be seen from the drawing, more than one strap B1-B2 can be used to lift different parts of the face. Obviously, also, only one can be used if desired. The provision of multiple loops allows for precise placement of the straps which will vary from person to person. Each of the B1-B2 straps is free to slide through its loop 1 as the head is turned. Element A and its loops provides a separate moving point for each strap used.

Element 4 in FIGS. 1 and 2 represents attachment of B1-B2 to a loop made of a hair extension. A hair extension, as is well known in the beauty art, is formed from synthetic hair which is heat fused to natural hair. This can be used at point 4 for a lift in the direction shown. The tabs are operable at all locations.

I claim:

1. A face lift device comprising a flexible band of material adapted to be adhesively attached to a human scalp, said band being flat on a first surface, and having a plurality of loops provided on the opposing surface; a two-piece strap wherein the first strap piece has a first end that is adapted to be adhesively attached to one side of the wearer's head or neck and the second and end of said first strap piece is shaped to permit it to pass through one of the loops on the said band, the second strap piece has a first end that is adapted to be adhesively attached to the other side of the head or neck of the wearer, and the second end of the second strap piece has a locking member through which the second end of said first strap piece enters after it has passed through said one of the loops, whereby the strap can slide relative to its loop as the head of the wearer moves.

2. A face lift device as claimed in claim 1 in which the first end of each of the said strap pieces which is adhesively attached to the wearer is provided with a tab which is adhesively attached to the skin of the wearer.

3. A face lift device as claimed in claim 1 which includes a plurality of straps spaced apart on said band whereby different portions of the face can be lifted by applying tension to the straps.

4. A face lift device as claimed in claim 2 which includes a plurality of straps spaced apart on said band whereby different portions of the face can be lifted by applying tension to the straps.

* * * * *